(12) United States Patent
Heiniger et al.

(10) Patent No.: US 7,892,212 B2
(45) Date of Patent: Feb. 22, 2011

(54) DRIVE DEVICE AND METHOD FOR ADVANCING AN ADVANCING ELEMENT

(75) Inventors: Hanspeter Heiniger, Lotzwil (CH); Stefan Jost, Muehleberg (CH); Roger Siegenthaler, Muensingen (CH); Heinz Wuthrich, Worblaufen (CH)

(73) Assignee: Roche Diagnostics International AG, Steinhausen (CH)

( * ) Notice: Subject to any disclaimer, the term of this patent is extended or adjusted under 35 U.S.C. 154(b) by 1096 days.

(21) Appl. No.: 10/564,115

(22) PCT Filed: Jun. 9, 2004

(86) PCT No.: PCT/EP2004/006221

§ 371 (c)(1),
(2), (4) Date: Aug. 16, 2006

(87) PCT Pub. No.: WO2004/110532

PCT Pub. Date: Dec. 23, 2004

(65) Prior Publication Data

US 2007/0088290 A1    Apr. 19, 2007

(30) Foreign Application Priority Data

Jun. 13, 2003    (DE) .............................. 103 26 766

(51) Int. Cl.
*A61M 5/00* (2006.01)
(52) U.S. Cl. ....................................... 604/208; 604/207
(58) Field of Classification Search .............. 604/218, 604/207–211
See application file for complete search history.

(56) References Cited

U.S. PATENT DOCUMENTS

| 5,244,465 A | * | 9/1993 | Michel ........................ 604/208 |
| 5,536,249 A | | 7/1996 | Castellano et al. |
| 5,728,074 A | | 3/1998 | Castellano et al. |
| 5,925,021 A | | 7/1999 | Castellano et al. |

FOREIGN PATENT DOCUMENTS

| DE | 198 38 862 A1 | 3/2000 |
| EP | 0 897 728 A | 2/1999 |
| JP | 10504729 | 5/1998 |
| WO | WO 94/13343 A | 6/1994 |
| WO | WO 98/01171 A | 1/1998 |

* cited by examiner

*Primary Examiner*—Kevin C Sirmons
*Assistant Examiner*—Deanna K Hall
(74) *Attorney, Agent, or Firm*—Dinsmore & Shohl LLP (57) ABSTRACT

A drive device for advancing an advancing element (2; 33) relative to a housing (1; 30) over a entire advancing distance (G) comprises a tensioning device having a tensioning element (3; 39) for tensioning a spring device (4). A predetermined distance (A) between the tensioning element (39) and the advancing element (33) or between the counter element (7) and the tensioning element (3) that engages with advancing element can be set according to the advancing of the advancing element (2; 33) by a partial advancing distance that is less than the entire advancing distance (G). According to a method for discharging a fluid product from a container (16) via an outlet (17), a plunger (18) is displaced inside the container (16) by means of a drive device provided with an advancing element (2; 33) and with a spring device (4), whereby the spring device (4) is tensioned by a tensioning device according to the advancing of the advancing element (2; 33) by a partial advancing distance.

12 Claims, 10 Drawing Sheets

DRIVE DEVICE AND METHOD FOR ADVANCING AN ADVANCING ELEMENT

The present invention relates to a drive device for advancing an advancing element and to a method for discharging a fluid product from a container, in particular in a device for blood glucose determination, in accordance with the preamble of claim 1.

In measurement methods, for example for determining the blood glucose values of a patient with diabetes, it is customary for a measurement probe with a dialysis membrane to be inserted into the patient's tissue, through which probe a measurement fluid is guided which exchanges, via the membrane, with the surrounding medium of the tissue. The measurement fluid can, for example, be introduced into the probe from an ampule via a line system. For this purpose, a drive device for discharging the fluid from the ampule is attached to the latter and, for example, drives a plunger in the ampule toward an outlet of the ampule. It is necessary to convey the measurement fluid through the fluid system of the probe at a constant determinable pressure in order to obtain reliable and reproducible measurement results. For this purpose, the drive device is, for example, equipped with a spring drive in which a pretensioned spring drives an advancing element relative to a housing of the device. The advancing element pushes the plunger in the ampule from its starting position to its end position at the outlet, the spring going from a compressed initial state to an expanded end state, and the advancing element advancing over the total advancing distance from the starting position to the end position. By setting the tensioning force of the spring, it is possible to determine the pressure generated in the ampule and at which the fluid is introduced into the line system of the probe.

In such drive devices and discharging methods, however, it is possible that the generated pressure subsides with increasing expansion of the spring, since the latter can apply a greater pressure force in a strongly compressed state than it can in a slightly compressed state. Moreover, it is necessary to use springs which have an expansion course corresponding to the total advancing distance of the advancing element in order to be able to discharge the fluid completely from the ampule. Such springs are in most cases rather long, and their length defines the total length of the drive device.

It is an object of the invention to make available a drive device for advancing an advancing element, which advances an advancing element with a settable and substantially constant force, has a compact structure, works with simple structural components, and is easy to operate.

It is a further object of the invention to make available a method for discharging a fluid product from a container, in which method the fluid product is discharged with constant pressure, the pressure during discharge can be regulated, and reliable discharge is ensured.

The objects of the invention are achieved by a drive device for advancing an advancing element in accordance with claim 1, and by a method for discharging a fluid product from a container. Advantageous embodiments are set forth in the dependent claims.

Accordingly, a drive device for advancing an advancing element relative to a housing of the device comprises a spring device for driving the advancing element, by means of which spring the advancing element can be advanced over a total advancing distance, i.e. over the distance by which the advancing element can be maximally displaced in relation to the housing. A helical spring is preferably used as the spring device. The spring device engages on a counter-element and on the advancing element which is movable relative to the counter-element inside the housing. The spring device does not necessarily have to be arranged directly on the counter-element or on the advancing element: it is also possible for the spring device to engage on the counter-element and/or advancing element via an intermediate element which transmits the force to the respective element. The helical spring can simply rest on the elements or it can also be securely connected to them.

According to the invention, a tensioning device with a tensioning element for tensioning the spring device is provided in the drive device. A predetermined distance is able to be set between the counter-element, which can be formed by the tensioning element, and the advancing element or between the counter-element and the tensioning element that engages on the advancing element. By setting the predetermined distance, i.e. by tensioning the spring device, the latter is placed under a defined pretensioning, as a result of which it exerts a defined tensioning force or pressure force on the advancing element or the counter-element as a function of the distance that has been set. To build up a tensioning force, the predetermined distance between the counter-element and the advancing element or the tensioning element is preferably chosen to be shorter than the length of the untensioned spring. However, it is also conceivable in principle to generate a tensioning force by means of the spring being extended, in which case a predetermined distance is chosen which is longer than the length of the untensioned spring. According to the invention, the distance can be set at the start of the advance and after an advance over a partial advancing distance, i.e. the tensioning device can tension the spring device during the advance of the advancing element without interrupting the force transmission and the advance. The partial advancing distance is shorter than the total advancing distance of the advancing element. The total advancing distance is preferably divided into several partial advancing distances, not necessarily all of the same length, such that a tensioning force can be retensioned and controlled several times during the advance of the advancing element over the total advancing distance. It is also possible to change the force during an advance or after a partial advancing distance and adapt it to new requirements by setting another predetermined distance.

In the method according to the invention for discharging a fluid product from a container through an outlet in the container, a plunger lying opposite the outlet inside the container is advanced in the direction of the outlet by a drive device with an advancing element and with a spring device. According to the invention, after the plunger has advanced by a partial advancing distance which is shorter than the total advancing distance, the spring device is tensioned by a tensioning device. To drive the plunger, a drive device is preferably used as has been described above, such that the plunger can be displaced toward the outlet by the advancing element of the drive device.

The ampule is connected to a housing of the drive device and the plunger is connected to the advancing element, such that the tensioning force or pressure force of the spring device is transmitted to the plunger, and consequently to the fluid product in the ampule, and a predetermined pressure is generated in the ampule. After the advancing element has been advanced by a partial advancing distance, the spring device is tensioned again, i.e. retensioned, by means of the predetermined distance between the counter-element and the advancing element or the tensioning element being set again. In this way, it is possible to avoid a drop in pressure caused by relaxation of the tensioning force due to less compression of the spring.

By means of the invention, during the advance of the plunger in the ampule over the total distance which is traveled by the plunger to the ampule outlet and which preferably corresponds to the total advancing distance of the advancing element, a constant pressure can be generated in the ampule, so that, for example in a blood glucose measurement probe, a reliably constant flow of the measurement fluid can be achieved or the pressure of the fluid can be adapted to a change in the flow speed. The invention, however, is not limited to the kind of areas described above, and instead it can be advantageously employed wherever a constant force is to be exerted on a slow moving element. Simple and inexpensive structural components can be used, and the assembling of the drive device is not complicated by the mechanical function of the drive device and does not take much time.

In a preferred embodiment of the invention, the housing of the drive device is sleeve-shaped. The advancing element is rod-shaped or sleeve-shaped and protrudes from the housing at one end of the housing. The counter-element can be formed, for example, by a projection of the housing protruding inward into the housing, by another element fixed relative to the housing, or also by the tensioning element. The tensioning element is preferably also sleeve-shaped and has an engagement surface which extends perpendicular to the advancing direction and which is provided for the spring device, i.e. the helical spring. The helical spring can, for example, be fitted between the engagement surface of the tensioning element and an engagement surface of the advancing element extending perpendicular to the advancing direction. Or the helical spring engages on a projection, secured to the housing, and on the engagement surface of the tensioning element which transmits the tensioning force to the advancing element.

For tensioning purposes, the tensioning element is preferably movable relative to the housing and to the advancing element in the direction of the counter-element, in order to be able to set the predetermined distance. The tensioning element is particularly preferably movable relative to the advancing element in only one direction parallel to the advancing direction and is fixed relative to the advancing element in an opposite direction. Thus, for setting the predetermined distance, the tensioning element can be moved relative to the advancing element or the counter-element and can at the same time transmit the tensioning force to the advancing element.

To set the predetermined distance, the tensioning device can comprise a rotary device with at least one rotary element that can turn relative to the housing. The rotary element is sleeve-shaped, for example, and protrudes at one end from the housing, the advancing element being advanced from the other opposite end of the housing. The tensioning element can have a thread, and the advancing element or the rotary element can have a mating thread which interacts with the thread of the tensioning element, so that, by means of a rotation of the rotary element, the tensioning element can be moved relative to the advancing element or the counter-element, and the predetermined distance can be set.

In a first preferred embodiment of the invention, the rotary element is fixed relative to the housing parallel to the advancing direction, but can turn relative to the housing, and forms the counter-element for the helical spring, i.e. it has an engagement surface for the helical spring. The tensioning element is secured against rotation relative to the rotary element, so that it follows the latter's rotation movement, but it can move relative to the rotary element parallel to the advancing direction. The tensioning element has an internal thread, with which it sits on an external thread of the advancing element. The advancing element is fixed in rotation relative to the housing so that, upon rotation of the rotary element, the tensioning element is turned relative to the advancing element and, because of the threads, moves parallel to the advancing direction, and a predetermined distance can be set between the tensioning element and the counter-element or the rotary element. It can be guided in the direction of movement by the threads and by a guide arrangement, for example on the rotary element or on the counter-element. The guide arrangement can also form the means of securing against rotation. A locking device is particularly preferably provided, by which means the rotary element is rotatable in only one direction or the rotation is transmitted to the tensioning element in only one direction. In this way, it is possible to ensure that, during tensioning, the tensioning element moves in only one direction relative to the advancing element in the direction toward the counter-element.

The helical spring is fitted between the tensioning element and the rotary element, which acts as counter-element. In the untensioned state, the helical spring is not compressed or is only slightly compressed, and the tensioning element bears on one end of the housing. When the rotary element is turned, the tensioning element is moved on the advancing element relative to the housing and into the inside of the housing and compresses the helical spring when a resistance force, for example a plunger of an ampule, bears on the advancing element. The tensioning force arising during the compression is transmitted to the plunger by the advancing element which is connected fixedly to the tensioning element in the advancing direction. The plunger in the ampule is advanced toward the outlet, the tensioning element moving back in the direction of the end of the housing, and the distance between tensioning element and counter-element increasing.

After the advancing element has traveled a partial advancing distance, renewed turning of the rotary element means that the tensioning element is moved back again in the direction of the counter-element, i.e. the rotary element, and the predetermined distance is set or a newly selected distance is set for another pressure in the ampule. When retensioning for the same predetermined distance between tensioning element and counter-element, the tensioning element is then moved by the length of the partial advancing distance on the advancing element in the direction of the counter-element, or rotary element. When retensioning, it is not necessary to interrupt the force transmission between helical spring and advancing element, and thus to the plunger, as a result of which the pressure on the fluid product in the ampule can be maintained continuously. The retensioning can be repeated as often as is necessary until the plunger has arrived at the outlet of the ampule and the advancing element has traveled the total advancing distance. Thereafter, the drive device can be removed from the ampule and made ready for a new application on a full ampule. To do this, the advancing element is guided back into a starting position, by means of the tensioning element being moved back on the advancing element.

In a second preferred embodiment of the invention, the tensioning element is secured against rotation relative to the housing, but is movable in the longitudinal direction of the housing and forms the counter-element of the drive device. The rotary element of the rotary device is fixed in the longitudinal direction relative to the housing, but is able to turn relative to the latter and has a rod-like or sleeve-like extension piece which extends through the housing with an external thread. The tensioning element or counter-element has an internal thread with which it engages in the external thread of the extension piece of the rotary element. The advancing element is sleeve-shaped, so that it is able to receive the extension piece of the rotary element, the tensioning element and the helical spring in its inside. The helical spring is fitted between an engagement surface of the advancing element, which engagement surface is perpendicular to the advancing direction, and the tensioning element as counter-element.

When the rotary element is turned relative to the housing, the tensioning element is moved on the extension piece of the rotary element in the direction toward the advancing element, i.e. the engagement surface of the advancing element for the helical spring, by which means the predetermined distance between the tensioning element or counter-element and the advancing element can be set. In doing this, it is guided in the movement direction by the threads and, for example, by guide arrangements on an inner surface of the housing. If an opposing force, for example a plunger of an ampule, bears on the advancing element, a tensioning force is generated in the helical spring. The tensioning force is transmitted to the plunger in the ampule, whereupon the advancing element is moved out from the housing in the advancing direction and the fluid product is forced through the outlet. In this process, the distance between the advancing element and tensioning element increases, and, after the advancing element has been advanced over a partial advancing distance, renewed turning of the rotary element means that the tensioning element is moved back on the extension piece of the rotary element toward the engagement surface of the advancing element, and the predetermined distance is set. The retensioning can be repeated until the tensioning element has moved from one end of the housing, or the extension piece of the rotary element, to the other end and the advancing element has traveled the total advancing distance. For renewed use of the drive device, the tensioning element can be moved back on the extension piece.

In this embodiment of the invention, it is particularly preferable for a locking device to be provided by means of which the advancing element can be fixed relative to the housing during the tensioning of the tensioning device. By fixing the advancing element, a force acts counter to the spring during tensioning, and a tensioning force can be built up without an ampule already being fitted on the housing and the advancing element fitted on the plunger. In the locked state of the advancing element, turning of the rotary element means that the tensioning element is moved toward the advancing element, the predetermined distance is set, and the tensioning force generated. To transmit the tensioning force to a plunger applied to the advancing element, the locking device is released, and a pressure can be built up in the ampule.

Within the varying distance between the tensioning element and the counter-element or between the advancing element and the counter-element, which distance arises as a result of the advance of the advancing element by a partial advancing distance, i.e. the varying length of the compressed helical spring, the spring is able to exert a constant pressure. The changes in length of the spring of these orders of magnitude do not cause any appreciable pressure fluctuations.

As a result of particularly substantial static friction between the plunger and an ampule wall, for example after a long period of storage of the ampule, it is possible that the tensioning force of the helical spring needed for a desired pressure in the ampule will not be sufficient to overcome this increased initial friction. It is therefore advantageous, in the drive device, to provide a striker device by which the plunger can be impacted at the start of the advance. The striker device can comprise an actuating device, for example a push button, and also a pusher element so that, upon actuation of the actuating device, i.e. by pressing the push button, the pusher element is driven in the advancing direction from the housing. In one embodiment, the push button can protrude from one end of the housing and have a continuation which protrudes through the housing from the opposite end of the housing. In another embodiment, the pusher element can be formed by the advancing element, which is connected to the push button. Pressing on the button is not intended to cause any great movement of the plunger, and instead a slight kick on the plunger suffices to overcome the increased initial static friction. A spring can be provided between the push button and the housing in order to bring the pusher element back into its starting position.

With the present invention, a constant pressure can be generated in the ampule by simple mechanical means. Compared to conventional drive devices, it is possible to use shorter helical springs and thus reduce the overall length of the drive device. The drive device can also be provided with a display which measures the number of rotations of the rotary device to make it easier to set a defined distance.

The invention is explained on the basis of illustrative embodiments and with reference to the drawing, in which.

Figure 1:
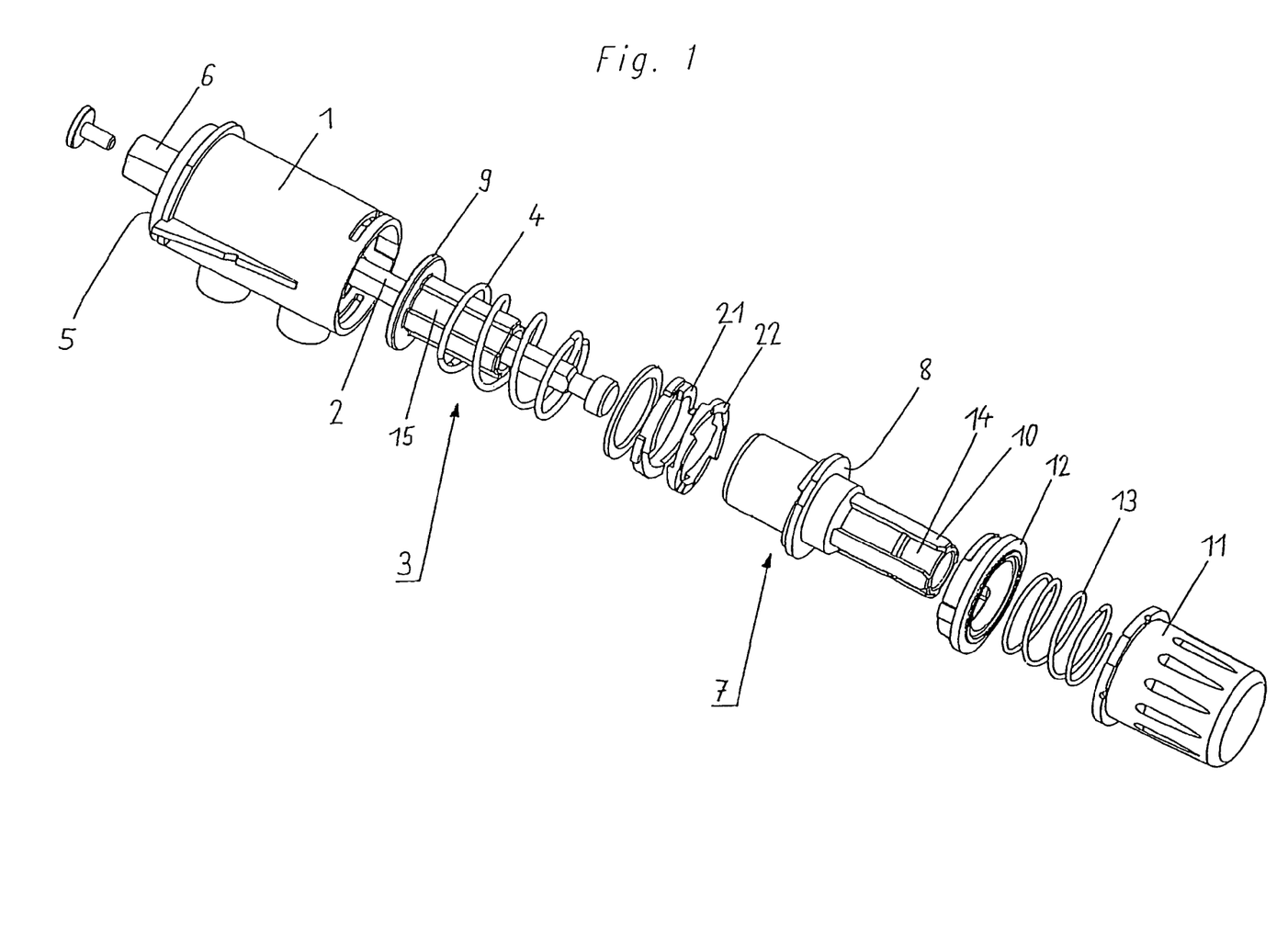
FIG. 1 shows a perspective exploded view of a first embodiment of a drive device according to the present invention.
Figure 2:
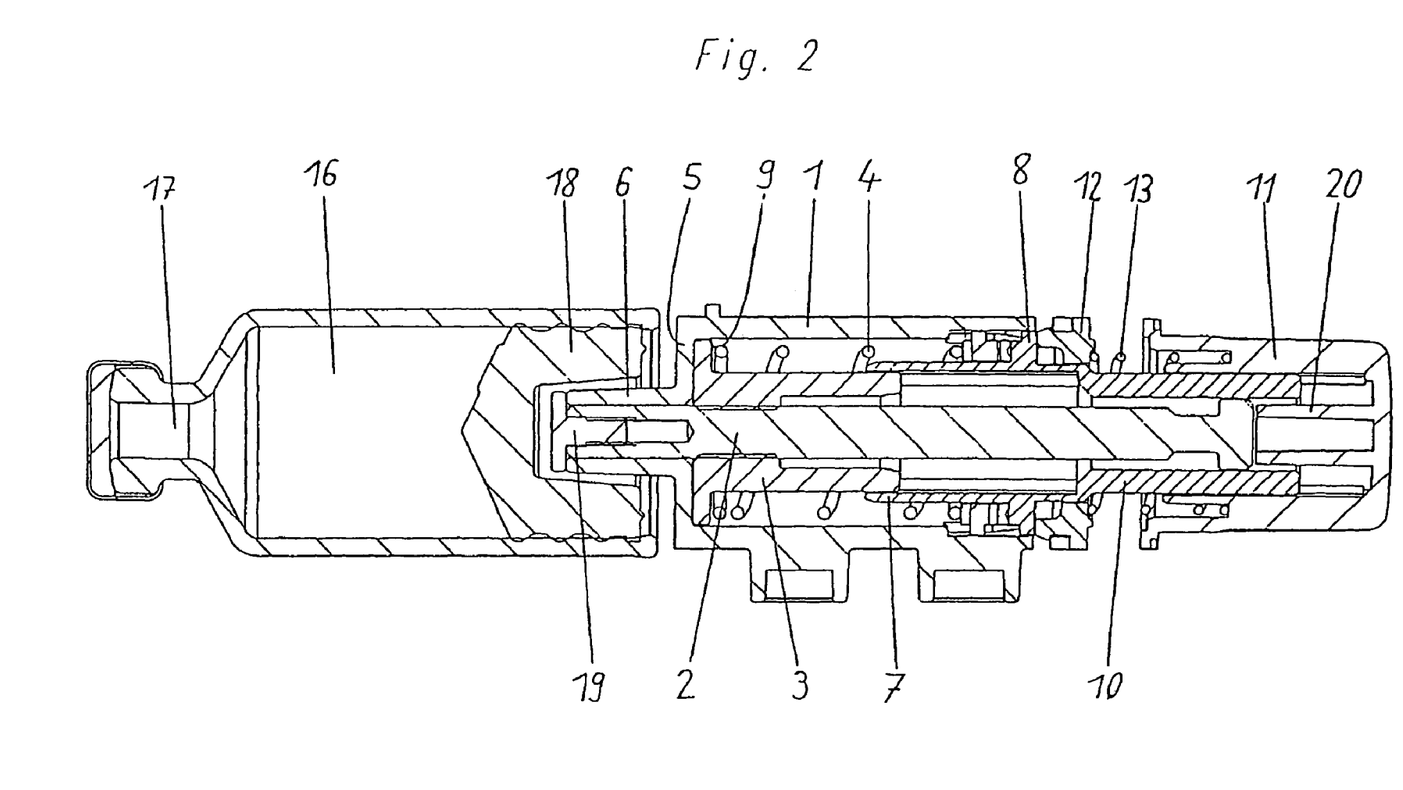
FIG. 2 shows a longitudinal section through the first embodiment of the drive device, with the spring device untensioned.

A drive device according to a first embodiment of the invention is shown in an exploded view in FIG. 1 and in an assembled state in FIG. 2. An advancing element in the form of a threaded rod 2, a sleeve-shaped tensioning element 3 and a spring device in the form of a helical spring 4 are fitted in a sleeve-shaped housing 1. At one end, the housing 1 has a wall 5 which closes off the housing 1 and which includes a passage for the advancing element 2. Provided around the passage there is a tubular continuation 6 onto which an ampule 16 can be fitted (see FIG. 2). A rotary element 7 is fitted into the housing 1, at the opposite end of the housing 1, and has a skirt 8 extending perpendicular to the circumferential direction of the housing 1. The skirt 8 forms an engagement surface for the helical spring 4. The rotary element 7 is held on the housing 1 by a retaining ring 12. At its end facing toward the wall 5 of the housing 1, the tensioning element 3 has an engagement surface 9 extending perpendicular to the circumferential surface of the housing 1 and provided for the helical spring 4. The helical spring 4 is fitted between the engagement surface 9 and the skirt 8.

The rotary element 7 has an extension piece 10 which protrudes from the housing 1 and on which a push button 11 is mounted. A spring 13 is fitted between the retaining ring 12 and the push button 11. On its circumferential surface, the extension piece 10 has guide grooves 14 which extend in the longitudinal direction and into which projections on an inner face of the push button 11 engage. The push button 11 is therefore secured against rotation in the circumferential direction relative to the extension piece 10.

On its outer jacket surface, the tensioning element 3 also has guide grooves 15 extending in the longitudinal direction. Projections on an inner jacket surface of the area of the rotary element 7 lying inside the housing 1 engage in the guide grooves 15. The tensioning element 3 can therefore be moved in the longitudinal direction relative to the rotary element 7, into the inside of the rotary element 7. At the same time, it is secured against rotation relative to the rotary element 7. The rotary element 7 is fixed in the longitudinal direction relative to the housing 1, but can be turned relative to the housing 1 by rotation of the push button. At one end of the housing, the threaded rod 2 is guided through the tubular continuation 6 and extends centrally through the housing in the longitudinal direction of the housing 1. An external thread is provided on the outer circumferential surface of the threaded rod 2. On the inner jacket surface of the tensioning element 3 there is an internal thread which interacts with the external thread of the threaded rod 2. By turning the tensioning element 3 relative to the threaded rod 2 by way of the rotary element 7, the tensioning element 3 can therefore be moved in the longitudinal direction on the threaded rod.

FIG. 2 shows the drive device in a starting position. An ampule 16 with an outlet 17 for a fluid product is mounted, via its end remote from the outlet 17, onto the continuation 6 of the housing 1 of the drive device. The continuation 6 partially extends into a recess of a plunger 18. The threaded rod 2 extends through the continuation 6 and, at its end facing in the direction of the plunger 18, it has a punch 19. In the starting position, the punch 19 of the threaded rod 2 is not in contact with the plunger 18 of the ampule 16.

Figure 3:
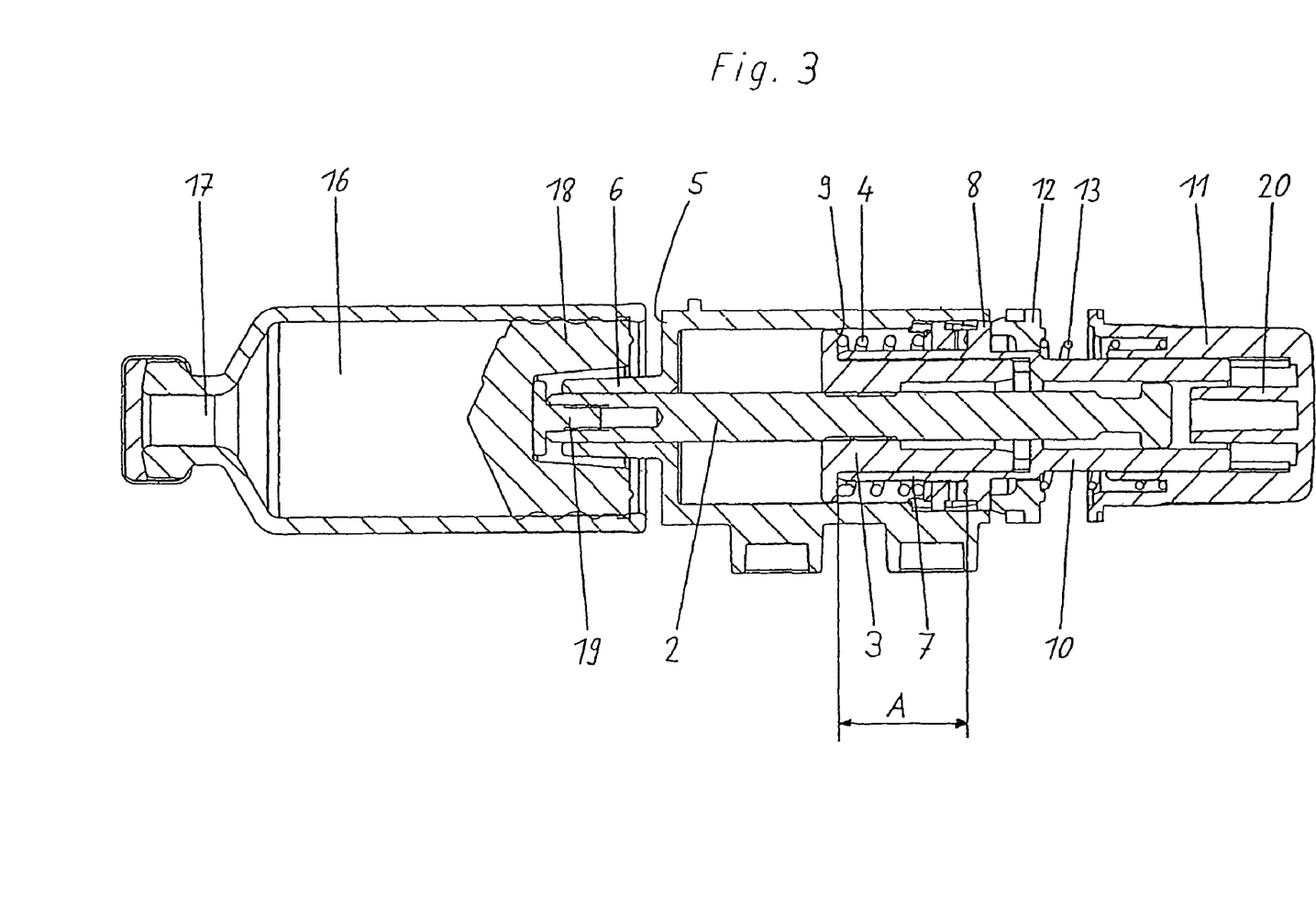
FIG. 3 shows a longitudinal section through the first embodiment of the drive device, with a predetermined distance set between tensioning element and counter-element.

In FIG. 3, a predetermined distance A is set between the engagement surface 9 of the tensioning element 3 and the skirt 8 of the rotary element 7. To do so, the push button 11 is turned relative to the housing 1 in one direction, as a result of which the rotary element 7 and thus also the tensioning element 3 are turned relative to the housing 1. The threaded rod 2 is secured against rotation relative to the housing 1. Upon rotation of the push button 11, the tensioning element 3 therefore moves about the threaded rod 2 and, by means of the interacting threads, is moved in the direction of the rotary element, which acts as counter-element for the helical spring 4. The engagement surface 9 of the tensioning element 3 is moved away from the wall 5 of the housing 1, and the helical spring 4 is compressed to a length corresponding to the distance A and builds up a tensioning force or spring force. The spring force acts counter to the skirt 8, fixed on the housing, and to the engagement surface 9 of the tensioning element, the latter transmitting the force to the threaded rod 2. Since the rotary element 7 with the skirt 8 is fixed relative to the housing, the spring force acts in the advancing direction of the threaded rod 2 or of the plunger 18 of the ampule 16. The threaded rod 2 with the punch 19 is initially advanced until the punch 19 bears on a surface of the piston 18 extending perpendicularly with respect to the circumferential surface of the ampule 16. The spring force can then be transmitted via the punch 19 to the plunger 18, which is thereby displaced inside the ampule 16, since the latter is fixed to the housing 1 of the drive device.

Figure 4:
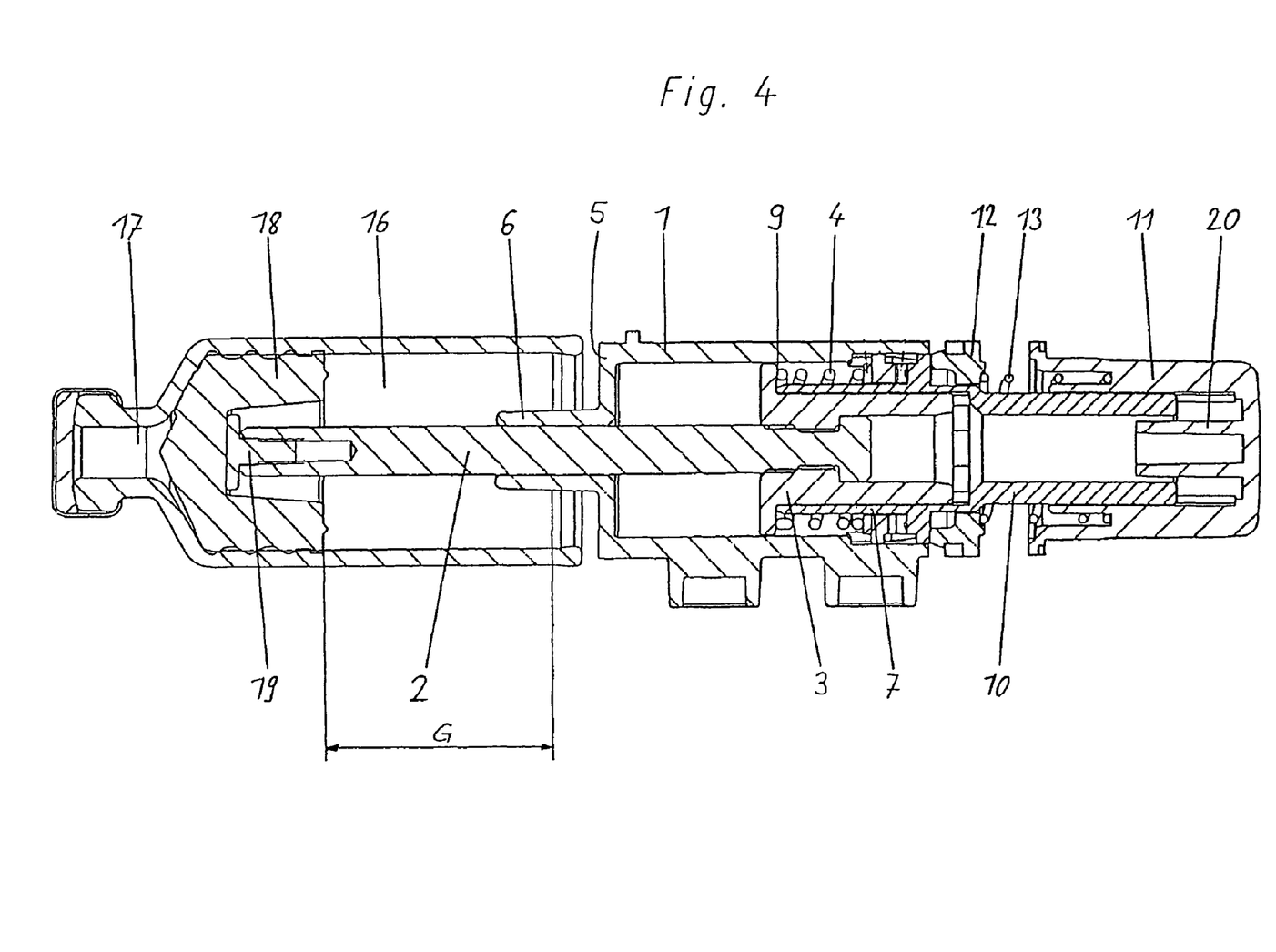
FIG. 4 shows a longitudinal section through the first embodiment of the drive device, with the advancing element advanced.

By means of the spring force, the threaded rod 2 is advanced together with the tensioning element 3 inside the housing 1 by a partial advancing distance, and the distance A increases, as a result of which the compression of the spring decreases. To compress the spring again and thereby tension the drive device once more, it is possible, by turning the push button 11, to move the tensioning element 3 in the direction of the rotary element 7 on the threaded rod 2. In doing so, the transmission of force to the plunger 18 is not interrupted. This procedure can be repeated after several partial advancing distances of the threaded rod 2 until the plunger 18 is advanced to the outlet 17 of the ampule 16, as is shown in FIG. 4. In this end position of the threaded rod 2, the threaded rod 2 and the plunger 18 have been advanced by the total advancing distance G. In the movement of the threaded rod 2, the latter is preferably guided by guide arrangements on the inner circumferential surface of the continuation 6 and by the tensioning element.

In the embodiment of the present invention depicted here, a striker device is also provided which includes the push button 11, the spring 13 and the threaded rod 2 as striker element. As can be seen from FIG. 2, the spring 13 is mounted between the retaining ring 12 and the push button 11, a distance being provided between the retaining ring 12 and that end of the push button 11 lying opposite it. The push button 11 has a centrally inwardly projecting web 20 which is oriented with respect to one end of the threaded rod 2 and makes contact with this end when the drive device is in a starting position.

Figure 5:
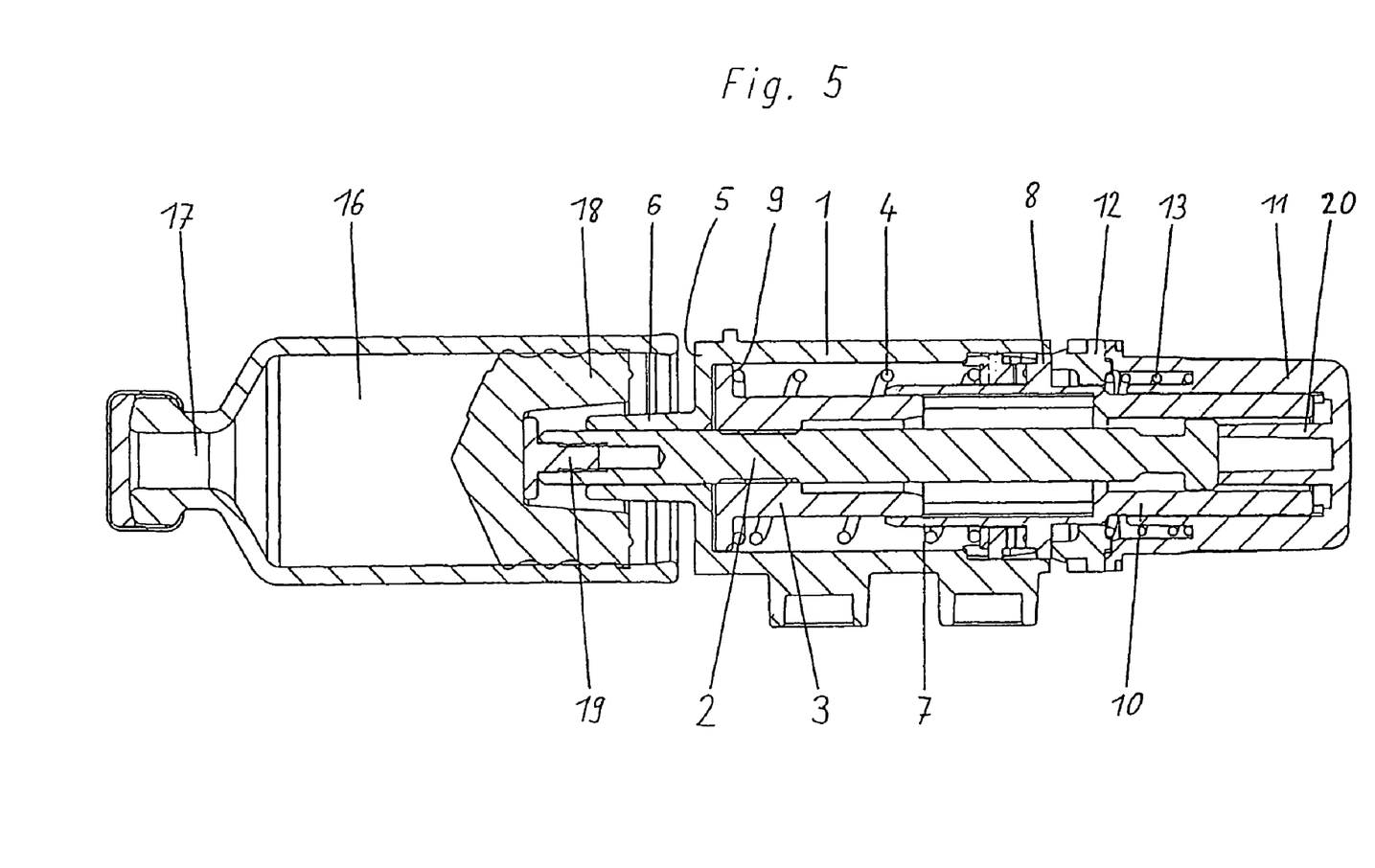
FIG. 5 shows a longitudinal section through the first embodiment of the drive device, with a striker device actuated.

In FIG. 5, the push button 11 is shown in a position in which it has been pressed in the longitudinal direction onto the housing 1. The threaded rod 2 is in this case pushed forward by the web 20 of the push button 11 in the advancing direction and transmits the impact via the punch 19 to the plunger 18 of the ampule 16. Static friction between the plunger 18 and the inside wall of the ampule 16 can be overcome by this impact. The push button 11 is moved away again in the longitudinal direction from the housing 1, counter to the advancing direction, by the spring force of the spring 13. After the release of the plunger 18, the driving of the plunger can be obtained by the spring force of the helical spring 4 of the drive device.

A locking arrangement is also provided in this embodiment, by a click-type lock with locking or clicking is possible after a discrete path of rotation is exceeded in one of the two directions of rotation. For this purpose, as is shown in FIG. 1, locking rings 21 and 22 are provided for transmitting the rotation movement of the rotary element 7 to the tensioning element 3. The locking rings 21 and 22 have mutually complementary steps on their surfaces extending perpendicular to the circumferential surface. On an inside edge of the skirt 8, there is also a ring which is stepped in the longitudinal direction and interacts with the locking rings 21 and 22. In one direction of rotation of the rotary element 7, the steps of the skirt 8 strike against steps of the ring 22, such that the ring 22 follows the rotation and is pulled with its opposite steps over the steps of the ring 21. This results in a locking or clicking action. In the other direction of rotation, steps on the ring 22 strike against steps on the ring 21, such that the ring 22 does not follow the rotation movement and the steps of the skirt 8 are pulled over the steps of the ring 22, once again resulting in a clicking action. Such a locking arrangement can also be configured as a safety measure against rotation overload, as is described in the application DE 104 40 393 from the Applicant.

In the first embodiment of the present invention as shown in FIGS. 1 through 5, the tensioning element 3, for building up a spring force in the helical spring 4, is moved by the rotation device counter to the advance movement and in the direction of the counter-element, i.e. the rotary element 7.

In a second embodiment, as shown in FIGS. 6 through 10, the tensioning element for building up the spring force is moved by the rotation device in the advance direction toward the advancing element. The second embodiment of the preset invention is shown in an exploded view in FIG. 6 and in its assembled state in FIG. 7a. A sleeve-shaped housing 30 is designed with a double wall, so that a space is formed between an outer wall 31 and an inner wall 32. The space is accessible at one end of the housing 30 at which the ampule 16 is attached, and it is closed off at the opposite end. The advancing element 33 in this embodiment is of substantially sleeve-shaped design and narrows at one end in such a way that an engagement surface 34 and a continuation 35 of reduced diameter are formed. The sleeve-shaped advancing element 33 is fitted with its sleeve wall 36 into the space of the housing 30 and is movable inside the latter along the longitudinal axis of the sleeve-shaped housing 30. A guide arrangement can be provided for guiding the longitudinal movement.

Figure 6:
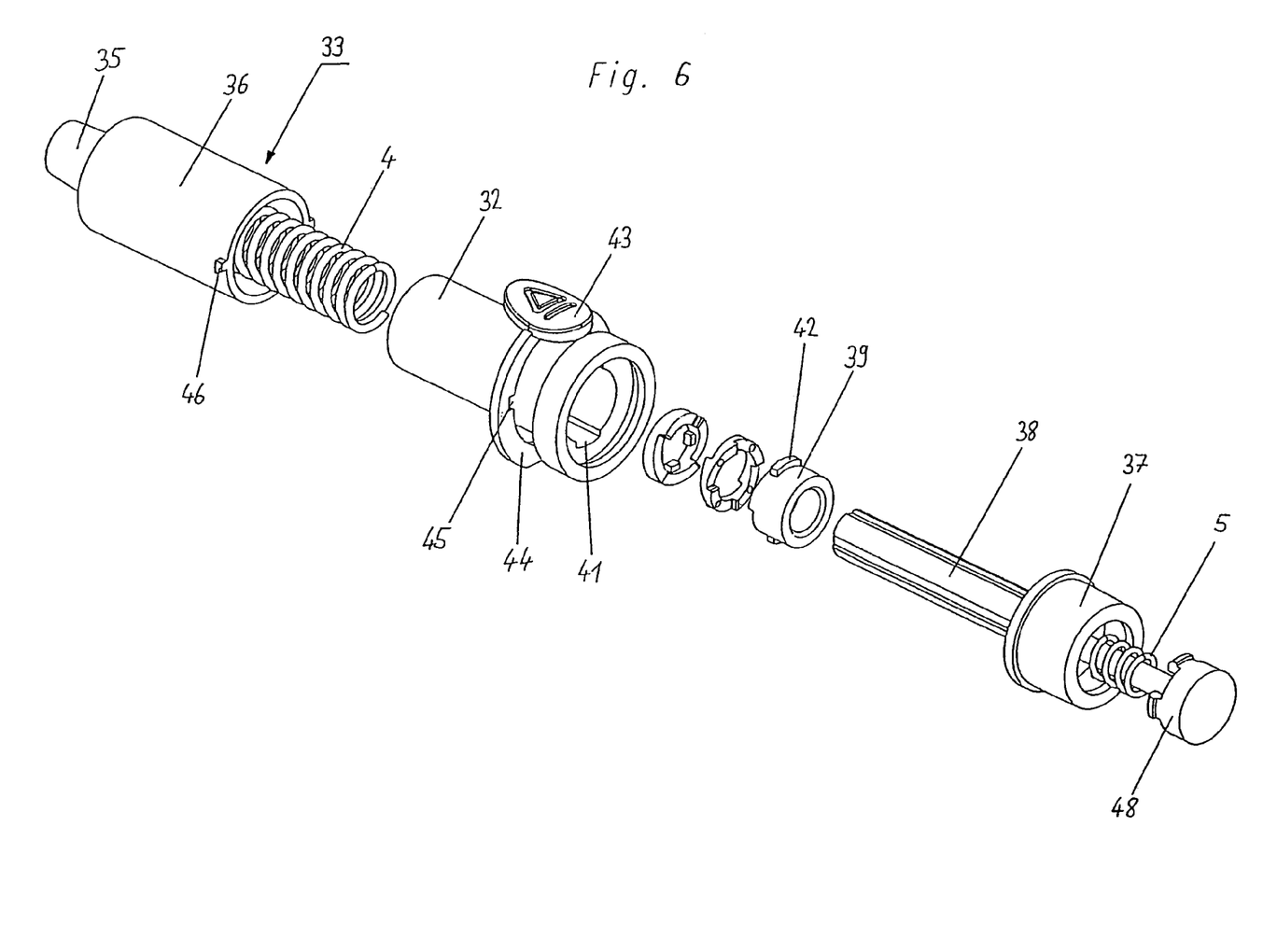
FIG. 6 shows a perspective exploded view of a second embodiment of a drive device according to the present invention.
Figure 7A:
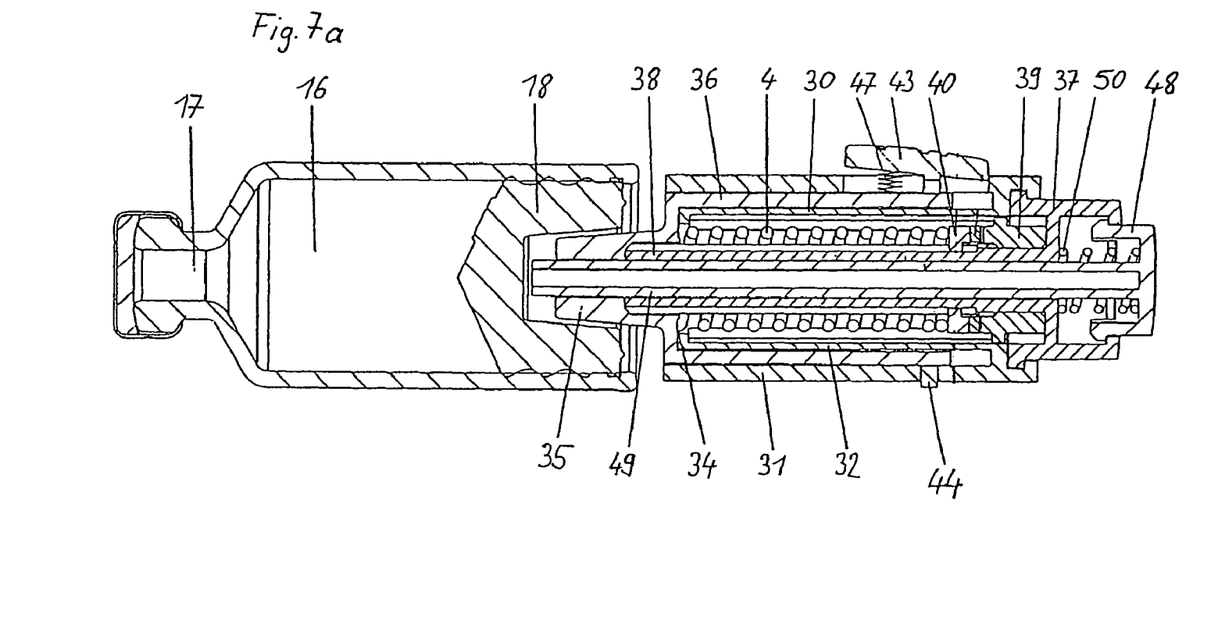
FIG. 7a shows a longitudinal section through the second embodiment of the drive device, with the spring device untensioned.

Provided inside the housing 30, i.e. inside the space delimited by the inner wall 32, there is a rotary element 37 with an extension piece 38, which extends centrally through the housing 30, a helical spring 4, and a tensioning element 39, which forms the counter-element for the helical spring 4. The rotary element 37 protrudes from the housing 30 at one end of the housing 30 which is remote from the end on which the advancing element 33 is fitted. The rotary element 37 is secured in the longitudinal direction on the housing 30 by means of complementary steps which engage in one another, such that the rotary element 37 is not movable in the longitudinal direction relative to the housing 30, but can turn relative to the latter. The extension piece 38 extends centrally through the inside of the housing 30 and ends at the opposite end of the housing 30 before the continuation 35 of the advancing element 33. An external thread is provided on the outer circumferential surface of the extension piece 38. The tensioning element 39 is also of a sleeve-shaped design and has, on its inner circumferential surface, an internal thread which interacts with the external thread of the extension piece 38. The tensioning element 39 has a surface 40 extending perpendicular to the advancing direction and is displaceable in the longitudinal direction of the housing 30 relative to the rotary element 37, i.e. on the extension piece 38. However, it is secured against rotation relative to the housing 30 by guide channels 41 on the inner circumferential surface of the inner wall 32 of the housing 30 and by projections 42 on the outer circumferential surface of the tensioning element 39, which engage in the guide channels 41. The guide channels 31 extend in the longitudinal direction of the housing 30 along the entire length of the inner wall 32, so that the tensioning element 39 is displaceable in the longitudinal direction along the entire length of the housing.

The helical spring 4 is arranged around the extension piece 38 between the engagement surface 34 of the advancing element 33 and the surface 40 of the tensioning element 39. At the end of the housing 30 from which the advancing element 33 protrudes, an ampule 16 is fitted onto the housing 30. The continuation 35 engages in a recess of the plunger 18 of the ampule 16.

The second embodiment of the present invention is shown in a starting position in FIG. 7a. The advancing element 33 is prevented, by a locking device, from moving relative to the housing 30 in the longitudinal direction of the housing. The locking device comprises a trigger 43 arranged on the circumference of the housing 30, with a ring 44 which encompasses the advancing element 33 and the inner wall 32 of the housing 30. The trigger 43 is movable perpendicular to the longitudinal direction of the housing 30. In its inner circumference, the ring 44 has recesses 45 provided for lugs 46 on the outer circumference of the advancing element 33.

Figure 7B:
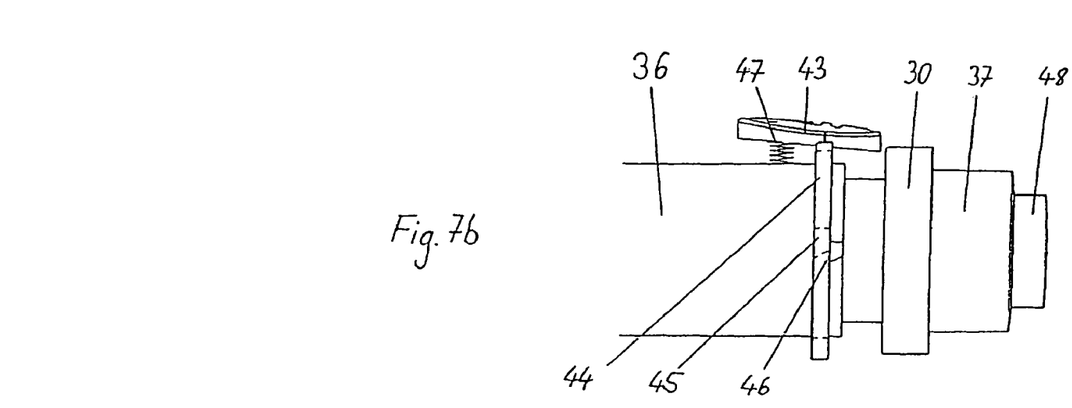
FIG. 7b shows a detail of a locking device of a drive device in the locked state.

In the locked state of the advancing element 33, the trigger 43 is pretensioned by a spring 47 in such a way that the lugs 46 of the advancing element 33 come to lie on an annular surface next to the recesses 45, specifically on a side facing away from the ampule end of the housing 30, as is shown in FIG. 7b. An advance of the advancing element 33 in the direction of the ampule is in this way prevented by the lugs 46 abutting the ring 44, and the advancing element 33 is locked.

Figure 8A:
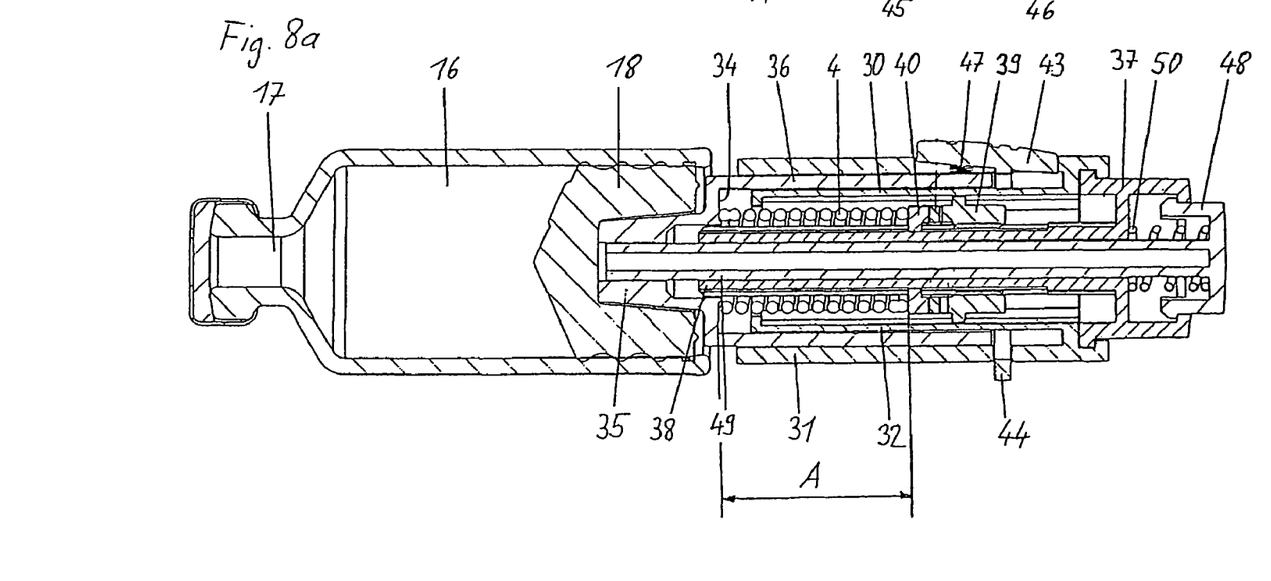
FIG. 8a shows a longitudinal section through the second embodiment of the drive device, with a predetermined distance set between tensioning element and advancing element.
Figure 8B:
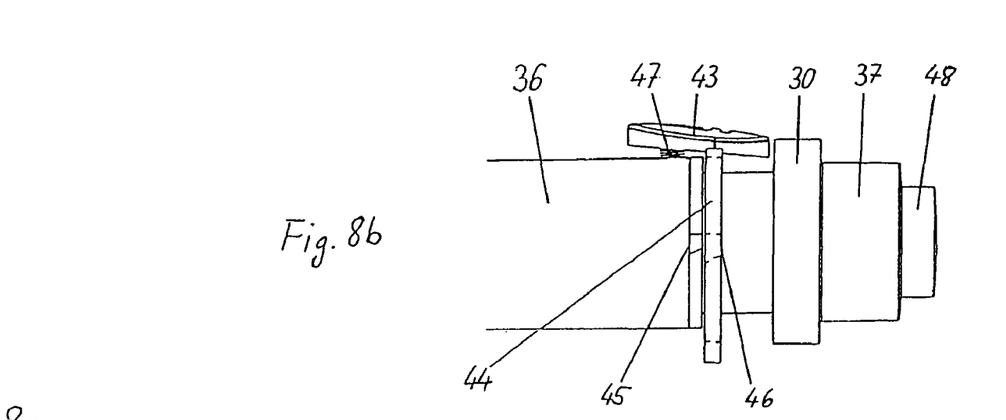
FIG. 8b shows a detail of a locking device of a drive device in the unlocked state.

FIG. 8a shows the tensioning of the drive device by the tensioning device, i.e. the tensioning element. By turning the rotary element 37 relative to the housing 30, the tensioning element 39 is displaced in the direction toward the advancing element 33, or the latter's engagement surface 34, by the interaction of the threads on the tensioning element 39 and on the extension piece 38 of the rotary element 37. According to the invention, the tensioning element 39 is moved as a counter-element for the spring toward the advancing element and a predetermined distance A is set between the tensioning element 39 and the advancing element 33, i.e. between the surface 40 and the engagement surface 34. The spring is thus compressed and a spring force is generated. In order to transmit the spring force to the plunger 18 of the ampule 16, the locking device is released by pressing the trigger 43 in the direction of the circumferential surface of the housing 30, so that the advancing element 33 is freed, as a result of the ring 44 being displaced perpendicular to the advancing direction such that the recesses 45 come to lie opposite the lugs 46 of the advancing element 33. By means of the spring force of the compressed helical spring 4, the advancing element 33 is moved in the advancing direction toward the plunger, and the lugs 46 move through the recesses 45, as is shown in FIG. 8b. After release of the advancing element 33, the trigger 43 can be brought back again into its starting position by the spring force of the spring 47.

Figure 9:
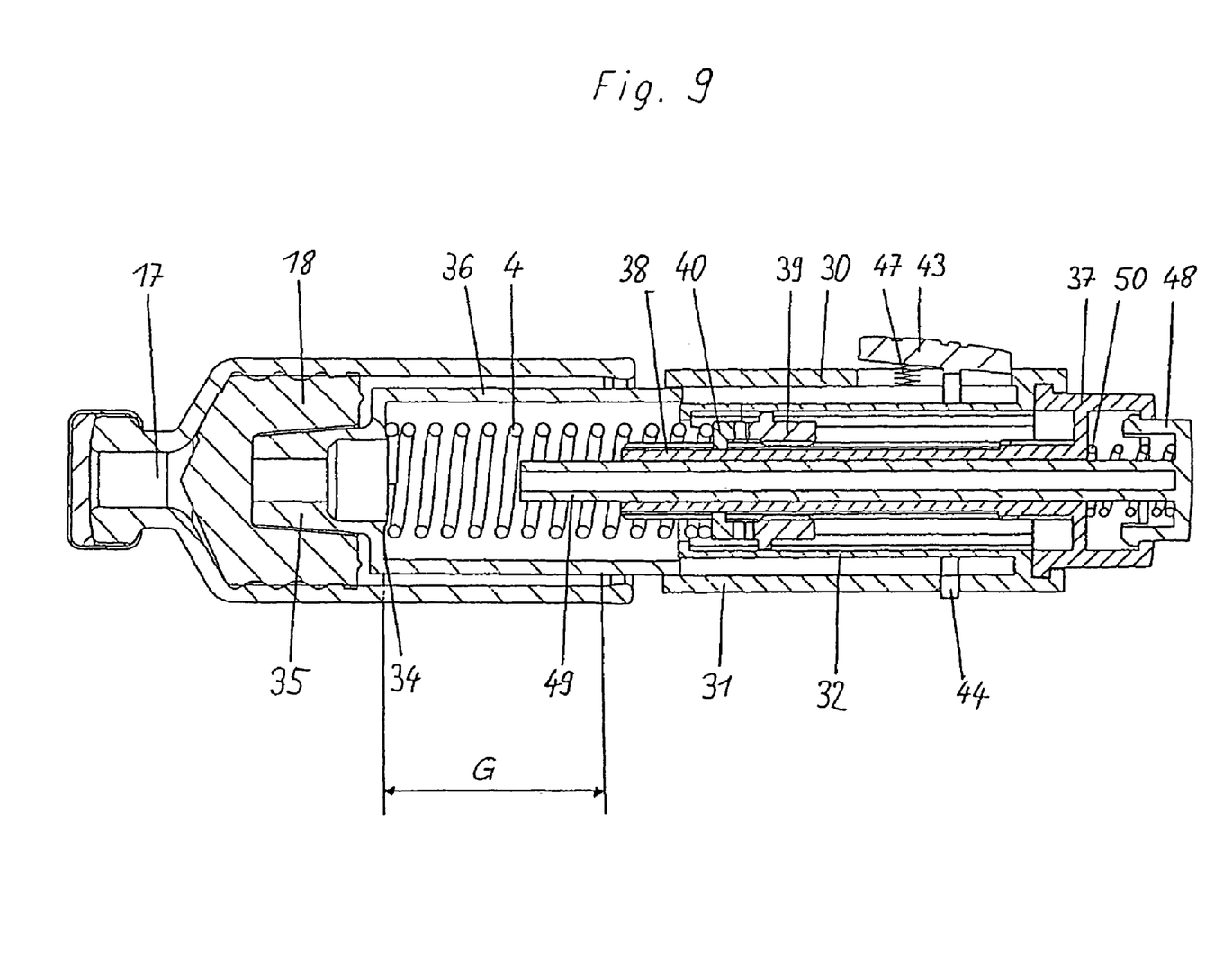
FIG. 9 shows a longitudinal section through the second embodiment of the drive device, with the advancing element advanced.

The released advancing element 33 is pressed, by the spring force of the helical spring 4, onto the plunger 18 of the ampule 16 such that the spring force is transmitted to the plunger 18 and the latter can be advanced toward the outlet 17 of the ampule 16. After a partial advancing distance of the advancing element 33, the drive device is tensioned by means of the rotary element 37 being turned and the tensioning element on the extension piece 38 being moved further toward the advancing element 33 in the advancing direction. The same predetermined distance A can be set again, or a new distance can be set. The tensioning of the drive device can be repeated several times until the plunger 18 reaches the outlet 17 of the ampule 16 and all the fluid has been discharged from the ampule, as is shown in FIG. 9. The tensioning element 39 has been advanced over the length of the extension piece 38 relative to the housing, and the advancing element has traveled the total advancing distance G.

Figure 10:
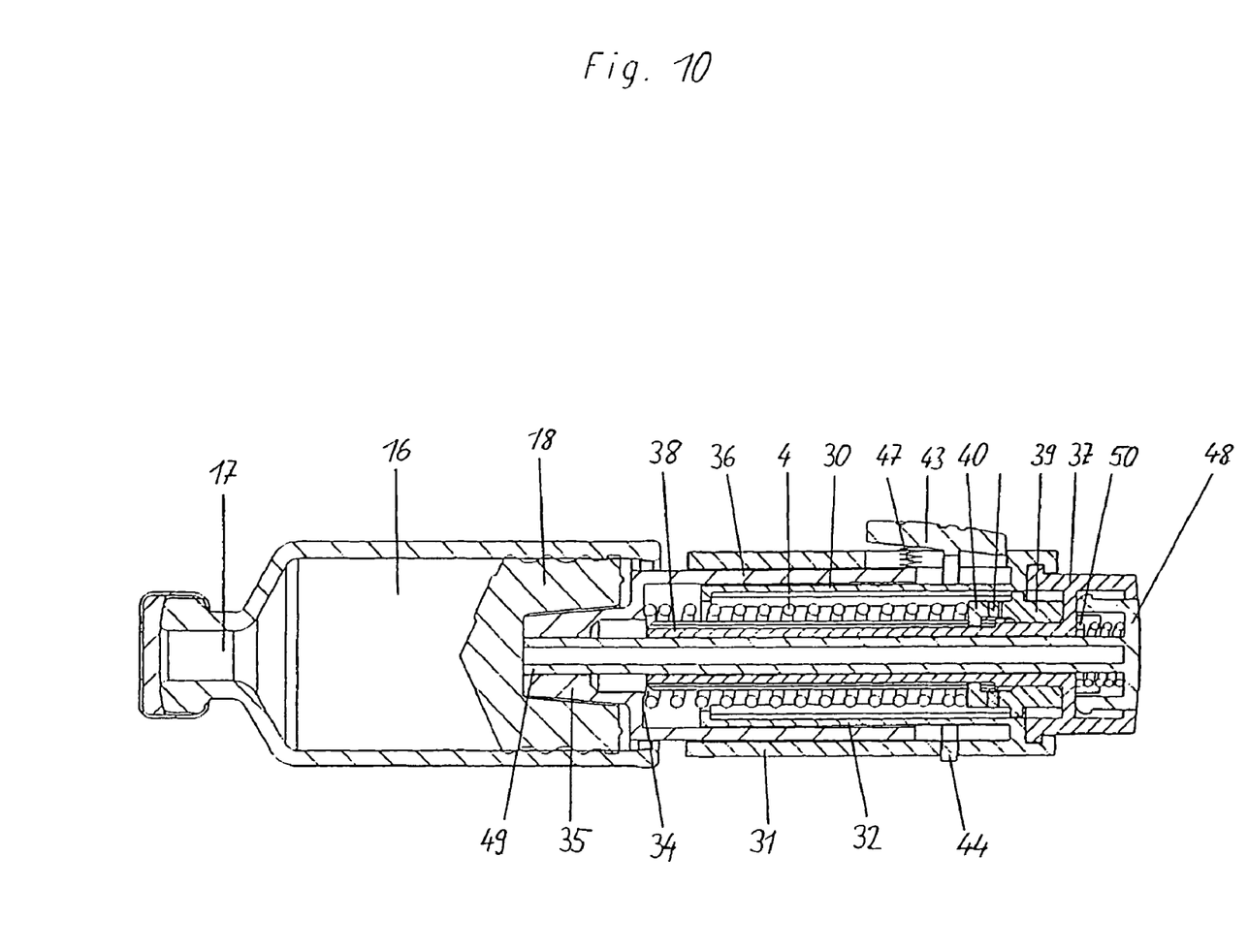
FIG. 10 shows a longitudinal section through the second embodiment of the drive device, with a striker device actuated.

In the second embodiment of the invention too, a striker device can be provided, as is shown in FIG. 10. The striker device comprises an actuating device in the form of a push button 48 which protrudes centrally from the housing 30 at one end of the housing. In the embodiment shown, the push button 48 is arranged on the end of the rotary element 37 protruding from the housing 30. From the push button 48, a passage 39 extends centrally through the housing 30 to the opposite end of the housing. The passage 49 can be rod-shaped or sleeve-shaped, for example, and extends through the inside of the extension piece 38 of the rotary element 37 and, in a starting position (see FIG. 7a), protrudes beyond the continuation 35 of the advancing element 33 in the direction of the plunger 18. A spring 50 holds the push button 48 in a pretension position in which the passage 49 is in a retracted setting.

After tensioning of the drive device and release of the locking device, the advancing element 33 is pushed by the spring force of the helical spring 4 onto the plunger 18 of the ampule, as is shown in FIG. 8a. If the spring force is insufficient to overcome an initially high static friction of the plunger 18 on the inner wall of the ampule 16, an additional impact on the plunger 18 can be exerted by the striker device. To do this, the push button 48 is pressed, as a result of which the passage 49 meets the plunger 18. The high static friction can be overcome in this way, so that the plunger can be advanced by the advancing element 33 solely through the spring force of the helical spring 4.

The present invention has been set forth on the basis of two illustrative embodiments. In the first illustrative embodiment, the advancing element of the drive device can be tensioned after the advance by a partial advancing distance, by means of the tensioning element of the tensioning device being displaced counter to the advancing direction on the advancing element in the direction of the rotary element, or counter-element. In the second embodiment, the tensioning of the drive device is effected by a movement of the tensioning element in the advancing direction toward the advancing element, which likewise moves in the advancing direction. In principle, other embodiments of a drive device of the present invention are conceivable as long as a predetermined distance between the elements which include the helical spring can be set by a tensioning device after an advancing element has been advanced over a partial advancing distance which is smaller than the total advancing distance.

LIST OF REFERENCE LABELS 1 housing
2 threaded rod
3 tensioning element
4 helical spring
5 wall
6 continuation
7 rotary element
8 skirt
9 engagement surface
10 extension piece
11 push button
12 retaining ring
13 spring
14 guide groove
15 guide groove
16 ampule
17 outlet
18 plunger
19 punch
20 web
21 locking ring
22 locking ring
30 housing
31 outer wall
32 inner wall
33 advancing element
34 engagement surface
35 continuation
36 sleeve wall
37 rotary element
38 extension piece
39 tensioning element
40 surface
41 guide channel
42 projection
43 trigger
44 ring
45 recess
46 lug
47 spring
48 push button
49 passage
50 spring
A distance
B total advancing distance

The invention claimed is:

1. A drive device for advancing an advancing element relative to a housing over a total advancing distance, comprising
a spring device for driving the advancing element in an advancing direction and
a tensioning element for tensioning the spring device, wherein
the spring device is tensioned between a counter-element and one of the advancing element and the tensioning element, and the advancing element is movable relative to the counter-element;
a first tension distance defined between the counter-element and the advancing element or between the counter-element and the tensioning element is set by translational movement of the tensioning element relative to the housing that tensions the spring device, the first tension distance corresponding to a first partial advancing distance of the advancing element;
the spring device is releasable to drive the advancing element the first partial advancing distance;
a second tension distance defined between the counter-element and the advancing element or between the counter-element and the tensioning element is set by an additional translational movement of the tensioning element relative to the housing that tensions the spring device, the second tension distance corresponding to a second partial advancing distance of the advancing element; and
each of the first partial advancing distance and the second partial advancing distance is shorter than the total advancing distance.

2. The drive device as claimed claim 1, wherein the spring device is formed by a helical spring which is tensioned between the counter-element and the advancing element or the tensioning element.

3. The drive device as claimed claim 1 wherein the first and second tension distances are smaller or greater than the length of the untensioned spring device.

4. The drive device as claimed in claim 1, wherein the tensioning element for tensioning the spring device is movable relative to the housing and the advancing element in the direction of the counter-element.

5. The drive device as claimed in claim 1, the tensioning element can be moved in the direction of the counter-element or of the advancing element by a rotary device with at least one rotary element rotatable relative to the housing.

6. The drive device as claimed in claim 1, wherein the tensioning element has a thread, and the advancing element or the rotary element has a mating thread which interacts with the thread of the tensioning element.

7. The drive device as claimed in claim 1, further comprising a striker with an actuating element and a pusher element is provided, the pusher element being able to be pushed in the advancing direction by actuation of the actuating element.

8. The drive device as claimed claim 7, wherein the pusher element is formed by the advancing element.

9. The drive device as claimed in claim 8, wherein the actuating element protrudes from one end of the housing and has a continuation which protrudes from the opposite end of the housing.

10. The drive device as claimed claim 1, further comprising a locking device for releasably fixing the advancing element relative to the housing upon tensioning of the tensioning device.

11. The drive device as claimed in claim 5, wherein the rotary element is fixed relative to the housing parallel to the advancing direction and forms the counter-element, and, by rotation of the rotary element, the tensioning element is movable relative to the advancing element counter to the advancing direction.

12. The drive device as claimed claim 5, wherein the tensioning element is secured against rotation relative to the housing and forms the counter-element, and, by rotation of the rotary element, the tensioning element can be moved in the advancing direction relative to the advancing element.

* * * * *